(12) United States Patent
Appelbaum

(10) Patent No.: US 9,867,947 B2
(45) Date of Patent: Jan. 16, 2018

(54) LABEL FOR A SYRINGE

(71) Applicant: Nicholas Appelbaum, Cape Town (ZA)

(72) Inventor: Nicholas Appelbaum, Cape Town (ZA)

( * ) Notice: Subject to any disclaimer, the term of this patent is extended or adjusted under 35 U.S.C. 154(b) by 0 days.

(21) Appl. No.: 14/907,335

(22) PCT Filed: Aug. 22, 2014

(86) PCT No.: PCT/IB2014/064022
§ 371 (c)(1),
(2) Date: Jan. 25, 2016

(87) PCT Pub. No.: WO2015/025300
PCT Pub. Date: Feb. 26, 2015

(65) Prior Publication Data
US 2016/0166776 A1   Jun. 16, 2016

(30) Foreign Application Priority Data
Aug. 22, 2013   (ZA) ................................ 2013/06327

(51) Int. Cl.
*A61M 5/315* (2006.01)
*A61M 5/14* (2006.01)
(Continued)

(52) U.S. Cl.
CPC ...... *A61M 5/31535* (2013.01); *A61M 5/1412* (2013.01); *A61M 5/31525* (2013.01);
(Continued)

(58) Field of Classification Search
CPC ................ A61M 5/3129; A61M 5/315; A61M 5/31531; A61M 5/31565;
(Continued)

(56) References Cited

U.S. PATENT DOCUMENTS

2002/0017784 A1\* 2/2002 Merry .................. G09F 3/0288
283/81
2002/0088131 A1\* 7/2002 Baxa ................. A61M 5/31525
33/494
(Continued)

FOREIGN PATENT DOCUMENTS

EP        1946787 A2    7/2008
GB        2364989 A     2/2002
JP        2007275609 A  10/2007

OTHER PUBLICATIONS

Merry et al., "A new infusion syringe label system designed to reduce task complexity during drug preparation," Anaesthesia. 62:486-91 (2007).
(Continued)

*Primary Examiner* — Lauren P Farrar
(74) *Attorney, Agent, or Firm* — Hoffman Warnick LLC

(57) ABSTRACT

A label (100) in the form of an accessory for a manufactured syringe is provided that has graduations corresponding to volumes within the syringe. The label (100) comprises a flexible generally rectangular elongate sheet (102) of material with adhesive provided on an operatively back surface thereof, the sheet (102) having two parallel major edges (104) extending along the length of the elongate sheet (102) and a first scale (106) visible from an operatively front surface (107) of the label (100) along one of the major edges (104) being a volume indication scale calibrated to align with an existing volume indication scale on the syringe. A second scale (108) is provided adjacent the volume indication scale (106), the second scale (108) being a scale that relates to a patient body weight scale calibrated so that a correct recommended dose of a medicament can be delivered to a patient of a given weight, either during administration of the medicament or during preparation of a mixture to be administered.

11 Claims, 4 Drawing Sheets

(51) Int. Cl.
 *A61M 5/31* (2006.01)
 *G09F 3/02* (2006.01)
(52) U.S. Cl.
 CPC ............... *A61M 2005/3126* (2013.01); *G09F 2003/023* (2013.01); *G09F 2003/0272* (2013.01)
(58) Field of Classification Search
 CPC ...... A61M 2005/3126; A61M 5/31535; A61M 5/1412; A61M 5/31525; G09F 2003/0272; G09F 2003/023
 See application file for complete search history.

(56) References Cited

U.S. PATENT DOCUMENTS

| | | |
|---|---|---|
| 2004/0024368 A1 | 2/2004 | Broselow |
| 2008/0195077 A1* | 8/2008 | Anatrini ................ B65C 9/067 604/404 |
| 2009/0139126 A1 | 6/2009 | Alipour |
| 2011/0042255 A1* | 2/2011 | Traboulsi ............. B65D 23/00 206/459.5 |
| 2012/0006712 A1 | 1/2012 | Kaplan et al. |
| 2013/0204225 A1* | 8/2013 | Creaturo ............. A61M 5/3129 604/506 |
| 2014/0207079 A1 | 7/2014 | Creaturo |

OTHER PUBLICATIONS

International Search Report and Written Opinion for PCT/IB2014/064022, dated Feb. 16, 2015, 9 pages.
EP Search Report for Corresponding EP Application No. 14837510 dated Apr. 10, 2017, 7 pages.

* cited by examiner

LABEL FOR A SYRINGE

FIELD OF THE INVENTION

This invention relates to syringes and syringe accessories.

BACKGROUND TO THE INVENTION

The preparation and administration of medicaments is a complex and frequently error-prone practice. The reason for this is that such preparation and administration requires that various variables relating to the medicament have to be taken into account, which may include, but are not limited to, a required volume of medicament for a given patient's body weight, the volume of required diluent in the case where the medicament requires dilution, or the rate at which a medicament, or medicament and diluent mixture, is required to be administered in the case of an infusion.

Medicament concentrations are commonly indicated in milligram per milliliter (mg/ml), whereas the required dosages of the medicaments are given in milligram per kilogram (mg/kg). Thus, for example, in a case where the medicament to be administered is dependent on the patient's body weight, a series of calculations have to be performed in order to determine the required volume of medicament in milliliters. The calculations in this case would include multiplying the patient's body weight by the required dosage, typically in milligrams per kilogram (mg/kg), which would then provide the total dose of medicament in milligrams (mg). The dose in milligrams (mg) then needs to be divided by the number of milligrams of medicament in each of one or more vials to determine the required volume in milliliters (ml), which can then be drawn into a syringe, and then administered.

The calculation is thus quite complex and may easily result in miscalculations, particularly where the medicament needs to be prepared in a high pressure emergency situation. Nevertheless, miscalculations can evidently also take place in a non-emergency context.

Certain emergency medicaments are administered on occasion for infrequently encountered indications, and even experienced medical providers may be unfamiliar with their use. In addition, certain medicaments may be ordinarily administered by persons who have no special training, such as the parent or caregiver of a patient, who may often not be able to perform the required complex calculations in order to determine the required volume of medicament.

For obvious reasons, the administration of a miscalculated required dosage of medicament can have a variety of detrimental consequences. On the one hand, these detrimental effects can occur as a result of incorrect dosing over a period of time. For example, long term underdosing of anti-infective agents may result in the development of drug resistance. On the other hand, such miscalculations can also have far more immediate effects, particularly when made in the anaesthetic and resuscitation context, where there may be devastating and immediately apparent consequences.

Currently, mass-produced syringes typically have only volume graduations printed on the outside of the syringe barrel. It has been proposed in the prior art to produce syringe labels for application to a syringe, in order to make information available on the outer surface of the syringe barrel, but the information typically includes only the medicament name as well as the medicament concentration.

Although stickers or other markings, which might be applied to some syringes, may be fairly effective in identifying the medicament type and concentration held within a syringe, these markings generally do not assist a user administering the medicament to determine the volume required to be administered, the amount of diluent required, where applicable, or the rate at which such medicament or medicament and diluent mixture should be administered. Furthermore, the markings often found on syringes are informal and non-standardised, having often been made by a practitioner by hand.

The applicant is aware of at least a limited number of syringes, where a pre-printed body weight scale corresponds to certain dosages of a particular medicament. However, the limited application of these pre-printed syringes does not remedy the difficult situation that exists in relation to all other medicaments to be administered in syringes that do not already have the additional information pre-printed thereon.

What is even more crucial, is that solutions to this problem that are to be effective in the developing world as well as the developed world, need to take account of the particular conditions and contexts of hospitals and clinics in poorly resourced environments, in which access to sophisticated equipment, and technology may be limited.

There is thus a pressing need for a solution that alleviates some of the abovementioned problems at least to some extent.

In this specification the term stopper is used to mean the plunger that is movable longitudinally within a barrel of the syringe.

SUMMARY OF THE INVENTION

In accordance with the invention there is provided a label in the form of an accessory for a standard manufactured syringe that has graduations corresponding to volumes within the syringe, the label comprising a flexible generally rectangular elongate sheet of material with adhesive provided on an operatively back surface thereof, the sheet having two parallel major edges extending along the length of the elongate sheet, characterized in that a first scale is provided so as to be visible from an operatively front surface of the label along one of the major edges, the first scale being a volume indication scale calibrated to align with an existing volume indication scale on the syringe, and a second scale is provided adjacent the volume indication scale, the second scale being a scale that relates to a patient body weight, the patient body weight scale being calibrated so that a correct recommended dose of the medicament can be delivered to a patient of a given weight, either during administration of a medicament or during preparation of a mixture to be administered, by aligning a stopper of the syringe with the patient weight indicated by the patient weight scale.

Further features of the invention provide for the label to also display the name and concentration of medicament to be held by the syringe, the recommended dose of that medicament, and the route by which it is to be administered.

Further features of the invention provide for the label to be colour-coded according to international colour coding systems used for labels to indicate the type of medicament to be held in the syringe; and for the relationship between the volume indication scale and the patient weight scale to be of a linear or non-linear relationship as determined by the recommended dosage characteristics of the medicament.

In a first embodiment of the invention the patient body weight scale is aligned with the volume indication scale so that the weight indications on the patient body weight scale increase in line with the volume indications on the volume indication scale.

In an alternative embodiment of the invention, the patient body weight scale is inversely aligned with the volume indication scale, so that the weight indications on the patient body weight scale decrease as the volume indications on the volume indication scale increase. The inverse scale allows for a medicament to be drawn into the syringe to a predetermined volume and the correct recommended dose of the medicament to be delivered to a patient of a given weight by aligning a stopper of the syringe with the inversely orientated patient weight scale.

An additional feature of the invention allows for one of the parallel major edges of the label to include a dilution assistance scale to indicate the volumes of medicament and diluent required for a recommended concentration of the mixture to be achieved. The dilution assistance scale may be two abutting columns labelled proximally to indicate the proportion of volume of medicament, and distally to indicate the proportion volume of diluent. This serves the purpose of indicating the relative amounts of medicament and diluent required to achieve the concentration necessary for the patient body weight scale to be accurate. The particular type of diluent is also indicated on the label (for example 5% dextrose water or physiological saline). In these labels, the concentration of medicament remains constant regardless of the weight of the patient. Larger patients simply receive larger volumes. These diluted mixtures may be administered with the aid of either scales described above.

Two further embodiments of the invention provide labels which assist a user in preparing a syringe-full of medicament or medicament and diluent mixture with a fixed mg/kg concentration by the use of an adapted dilution scale. In such embodiments the total amount of medicament required is variable, depending on the weight of the patient, and this is indicated on the adapted dilution scale.

In a first of such further embodiments, the label includes a bolus scale, which may be used to administer a constant dose of medicament or medicament and diluent mixture in a bolus fashion. In this embodiment, the patient weight scale is used to draw a required volume of medicament into the syringe, depending on the patient's body weight, and the syringe may then be filled with a diluent for a fixed recommended mg/kg concentration, which may then be administered according to the fixed volumes indicated by the bolus scale. Unlike previous embodiments, in this embodiment it is the per kilogram total concentration which is variable.

In the second of such further embodiments, the label may include an administration assistance table for the determination of a required rate of administration of a concentration of medicament for a given patient weight. In this embodiment, the patient weight scale is used to draw a required volume of medicament into the syringe and the syringe may then be filled with a diluent for a fixed recommended mg/kg concentration, which may then be administered according to a required rate of administration determined by the administration assistance table. The fixed concentration of medicament in the syringe allows the user to use the same administration assistance table to determine the required rate at which to run an infusion of the contents of the syringe in order to achieve a required mcg/kg/min dose target, irrespective of the weight of the patient. Running an infusion is most often achieved using a syringe pump or syringe driver, but should these devices be unavailable (in resource-limited settings) the mixture may be run through a standard inline infusion pump apparatus after being introduced into a suitable vessel with the assistance of a syringe having a label according to this invention applied to it.

Further features of the invention provide for the label to be opaque or transparent, preferably partially transparent so as to assist with the alignment of the syringe stopper with the patient weight scale. Alternatively, where the label is opaque, a window may be cut into the label to facilitate alignment of the syringe stopper with the patient weight scale.

The invention extends to a syringe having an accessory according to the invention applied to it, the label carrying indicia including a first scale, being a volume indication scale, and a second scale adjacent the volume indication scale, the second scale being a patient body weight scale, the patient body weight scale being calibrated so that the correct recommended dose of the medicament is delivered to a patient of a given weight by aligning a stopper of the syringe with the patient weight indicated by the patient body weight scale.

DETAILED DESCRIPTION WITH REFERENCE TO THE DRAWINGS

Figure 1:
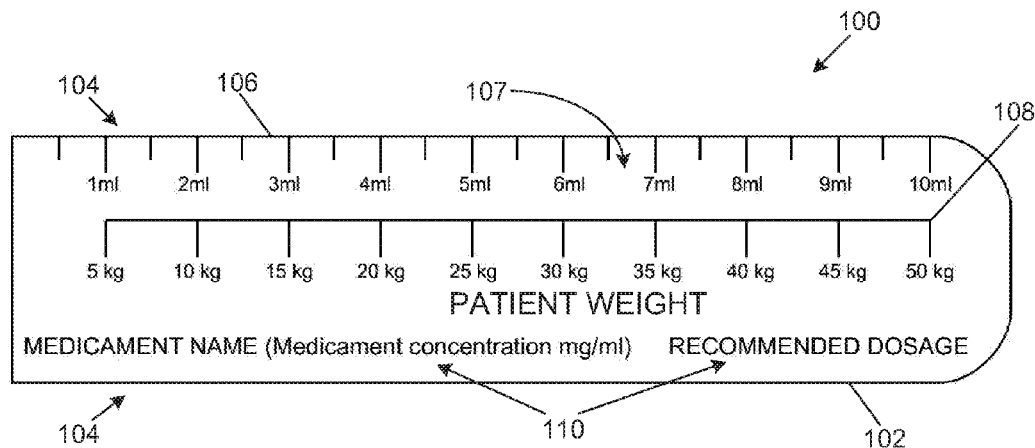
FIG. 1 illustrates a first embodiment of a label in the form of an accessory for a syringe in accordance with the invention.
Figure 4:
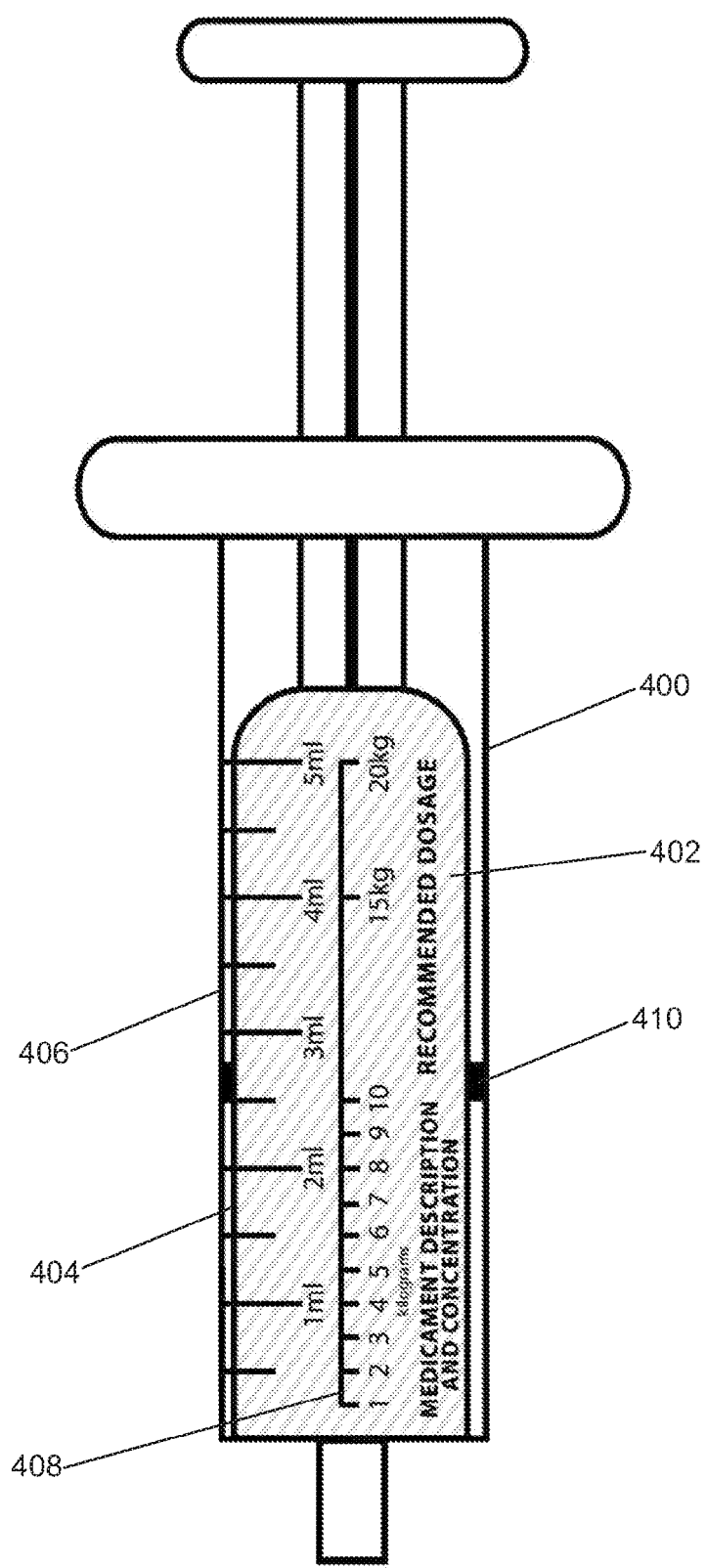
FIG. 4 illustrates an example of the label type illustrated in FIG. 1 having been affixed to a syringe, in which the label is opaque.
Figure 5:
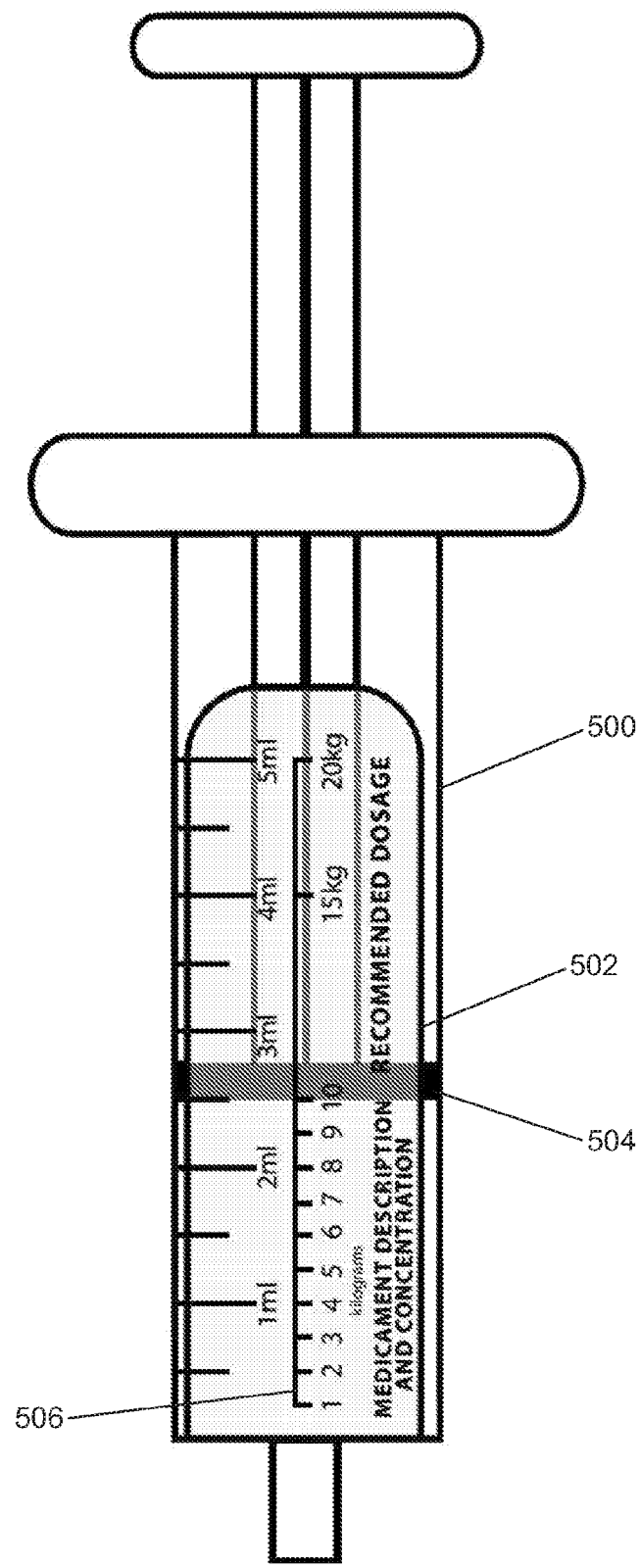
FIG. 5 illustrates an example of the label type illustrated in FIG. 1 having been affixed to a syringe, in which the label is at least partially transparent.

FIG. 1 illustrates a first embodiment of a label (100) in the form of an accessory for a syringe in accordance with the invention. The label (100) comprises a flexible generally rectangular elongate sheet (102) of material with adhesive provide on an operatively back surface (not shown) thereof. The sheet (102) has two parallel major edges (104) extending along the length thereof, and includes a first scale (106) so as to be visible from an operatively front surface (107) of the label (100) along one of the edges (104) and a second scale (108) adjacent the first scale (106). The first scale (106) is a volume indication scale, which is calibrated to align with an existing volume indication scale on a syringe, as is illustrated in FIGS. 4 and 5. The second scale (108), is a patient body weight scale, and is calibrated so that the recommended dose of a medicament is delivered to a patient of a given weight by aligning a stopper of the syringe with the patient weight indicated on the patient body weight scale (108). In the embodiment illustrated in FIG. 1, the relationship between the volume indication scale (106) and the patient body weight scale (108), is a linear relationship which is determined by the recommended dosage characteristics of the medicament to be drawn into the syringe.

The label (100) provides for a display (110) on which is displayed a type of medicament held within the syringe, the concentration of the medicament, the recommended dosage of the medicament, as well as the recommended route of administration. It is envisaged to have the label (100) colour-coded according international colour coding systems typically used to indicate different medicaments, thereby reducing the risk of accidentally injecting a wrong medicament. Furthermore, the information displayed preferably complies with additional safety features commonly employed in the medical industry, such as exaggerated-prefix lettering of similar sounding medicaments, or barcoding.

Figure 2:
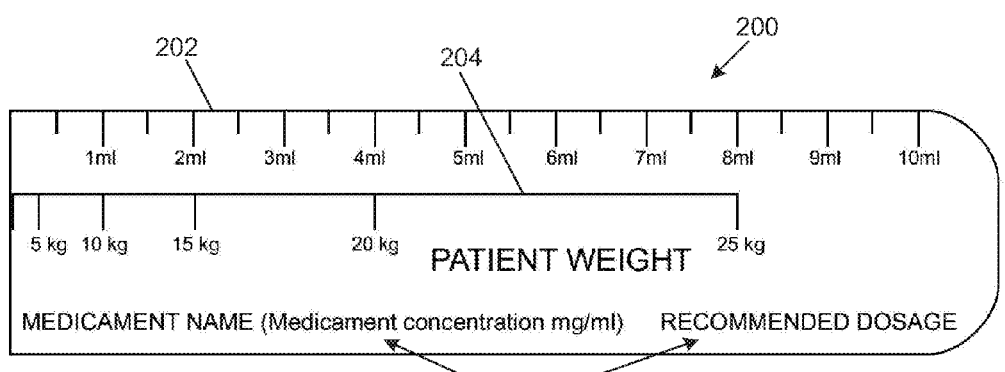
FIG. 2 illustrates a second embodiment of a label in the form of an accessory for a syringe in accordance with the invention, demonstrating a non-linear body weight scale.

FIG. 2 illustrates a second embodiment of a label (200) in the form of an accessory for a syringe according to the invention. The label (200) of this embodiment is substantially similar to the label (100) illustrated in FIG. 1, except that in this embodiment, the relationship between the volume indication scale (202) and the patient body weight scale (204) is of a non-linear relationship. The required dose of medicament for a given patient depends on various factors, such as not only the body weight of the patient, but factors relating to drug metabolism and excretion (for example age or renal dysfunction). Therefore the dose and thus volume of medicament required may increase or decrease exponentially or according to some other non-linear relationship. Similarly as the label (100) illustrated in FIG. 1, the label (200) illustrated in FIG. 2 provides for a display (206) to display a type of medicament held within the syringe, the concentration of the medicament, recommended dosage of the medicament, as well as the recommended route of administration.

Figure 3:
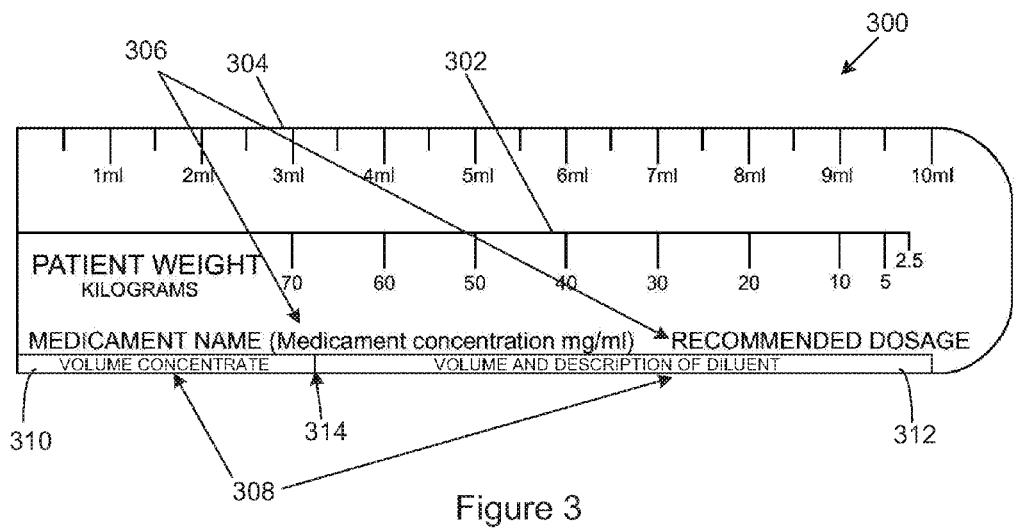
FIG. 3 illustrates a third embodiment of a label in the form of an accessory for a syringe in accordance with the invention, demonstrating a dilution assistance scale as well as an inverse body weight scale.

FIG. 3 illustrates a third embodiment of a label (300) in the form of an accessory for a syringe according to the invention. The label (300) of this embodiment is again similar to the labels (100, 200) illustrated in FIGS. 1 and 2, however, in this embodiment the patient body weight scale (302) is inversely aligned with the volume indication scale (304) so that the weight indications on the patient body weight scale (302) decrease as the volume indications on the volume indication scale (304) increase. The inverse patient body weight scale (302) will allow for the dilution of a medicament with a diluent by drawing the required volume of each substance into the syringe until the syringe is filled, and then administering the required amount of the mixture according to the body weight of the patient, by administering the mixture until the stopper of the syringe is aligned with the weight indication matching the body weight of the patient on the patient body weight scale (302).

The label (300) again provides for a display (306) to display a type of medicament held within the syringe, the concentration of the medicament, the recommended dosage of the medicament, as well as the recommended route of administration.

Furthermore, the label (300) further includes a dilution assistance scale (308) to indicate the volume of medicament and diluent required for a recommended concentration of medicament and diluent mixture. The dilution assistance scale (308) is in the form of two abutting columns (310, 312) that are labelled to indicate the proportion volume of medicament and the proportion volume of diluent required to achieve the concentration necessary for the patient body weight scale (302) to be accurate. It is envisaged that the particular type of diluent is also indicated on the label, for example 5% dextrose water or physiological saline, so as to avoid the mixing of an incorrect diluent with a particular medicament.

In use, the correct volume of the mixture is achieved by drawing into the syringe the medicament until the stopper of the syringe aligns with the indicated volume required of the medicament (314), which is where the two columns (310, 312) meet, and thereafter doing the same with the diluent as required, typically until the syringe is filled to the indicated total volume.

It will be appreciated that the use of the dilution assistance scale will ensure that the medicament or medicament and diluent concentration will, if properly employed, always be constant and the appropriate volume thereof is then administered according to the patient weight, by aligning the stopper with the patient weight as indicated on the patient weight scale. Larger patients will thus simply receive larger volumes.

Of course, similar to the label (200) illustrated in FIG. 2, the label (300) illustrated in FIG. 3 could also be provided with a patient weight scale (302) having a non-linear relationship to the corresponding volume indication scale (304).

It is further envisaged that the labels (100, 200, 300) are either opaque or at least partially transparent, preferably partially transparent, so as to facilitate accurate alignment of the syringe stopper with the patient weight indication on the patient body weight scale (108, 204, 302). This feature is more clearly illustrated in FIGS. 4 and 5. In the event of the labels (100, 200, 300) being opaque, they may be provided with a window, preferably adjacent the patient body weight scale (108, 204, 302), so as to enable accurate alignment of the stopper.

FIG. 4 illustrates a syringe (400) to which a label (402) in accordance with the embodiment illustrated in FIG. 1 has been affixed. The label (402) includes a volume indication scale (404) which is calibrated to align with an existing volume indication scale (406) on the syringe (400). The label (402) further includes a patient body weight scale (408) adjacent the volume indication scale (404), which is calibrated so that the required volume of a medicament may be administered given the body weight of a patient.

In use, and as illustrated in FIG. 4, once the body weight of a patient has been determined, the medicament is simply drawn into the syringe (400) until a stopper (410) of the syringe (400) is aligned with the weight indication on the patient body weight scale (408), and then administered. Alternatively, although not indicated in FIG. 4, the label affixed to the syringe may be in accordance with the embodiment illustrated in FIG. 3, thus where the patient weight scale is inversely aligned with the volume indication scale. In this case, the medicament and/or diluent are drawn into the syringe until the syringe is filled, preferably by using the dilution assistance scale provided on the label, and the mixture is then administered by moving the stopper until it aligns with the indication on the body weight scale matching the body weight of the patient.

It will be appreciated that the correct use of a label in accordance with the invention will eliminate the need for performing the complex calculations typically required to determine a required volume of medicament to be administered, thus substantively decreasing the risk of administering the incorrect dosage, as well as decreasing the time required to prepare such a dose. Furthermore, by providing such labels with any medicament that is administered by means of a syringe, even untrained users will be able to easily and effectively administer medicaments to patients.

FIG. 5 illustrates a syringe (500) to which a label (502) in accordance with the embodiment illustrated in FIG. 1 has been affixed. The label (502) is substantially similar to the label (402) illustrated in FIG. 4, except that the label (502) in FIG. 5 is at least partially transparent. It will be appreciated that the transparency of the label (502) substantially increases the ease of aligning the stopper (504) of the syringe (500) with the weight indication on the patient body weight scale (506) that matches the body weight of the patient.

Figure 6:
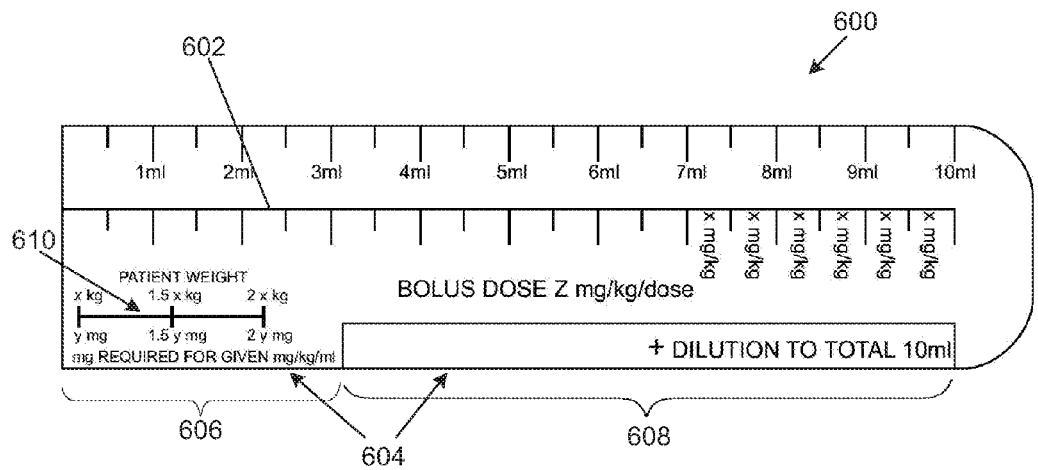
FIG. 6 illustrates a fourth embodiment of a label in the form of an accessory for a syringe in accordance with the invention, demonstrating an adapted dilution scale as well as a bolus scale; and, FIG. 7 illustrates a fifth embodiment of a label in the form of an accessory for a syringe in accordance with the invention, demonstrating an adapted dilution scale as well as an infusion administration assistance table.

FIG. 6 illustrates a fourth embodiment of a label (600) in the form of an accessory for a syringe in accordance with the invention. In this embodiment, the label (600) includes a bolus scale (602) which indicates constant bolus volumes of a given concentration of medicament or medicament and diluent mixture, in for example, milligrams per kilogram. The label (600) further includes an adapted dilution scale (604) on which is displayed the total number of milligrams of medicament (606) required as well as the volume of diluent (608) required. Furthermore, the required medicament and diluent volumes will be calibrated to the patient weight scale (610), so that in order to prepare a correct mixture of medicament and diluent for a given patient weight, the medicament is drawn into the syringe according to the patient's body weight indicated on the patient body weight scale (610) and then drawing the applicable amount of diluent into the syringe. The required diluent may either be the volume required to fill the syringe, or a specific amount of diluent to obtain a specific concentration depending on the patient body weight and medicament concentration.

Once the correct amount of medicament or mixture of medicament and diluent has been drawn into the syringe, the medicament or mixture can be administered according to the bolus scale (602). The bolus scale will preferably be used where bolus amounts are administered to the patient. It will be appreciated that due to the concentration of medicament in the syringe being dependent on the patient body weight, the volume or bolus amount will stay constant for a given weight. Similarly, once the mixture has been prepared, the concentration will stay constant.

Figure 7:
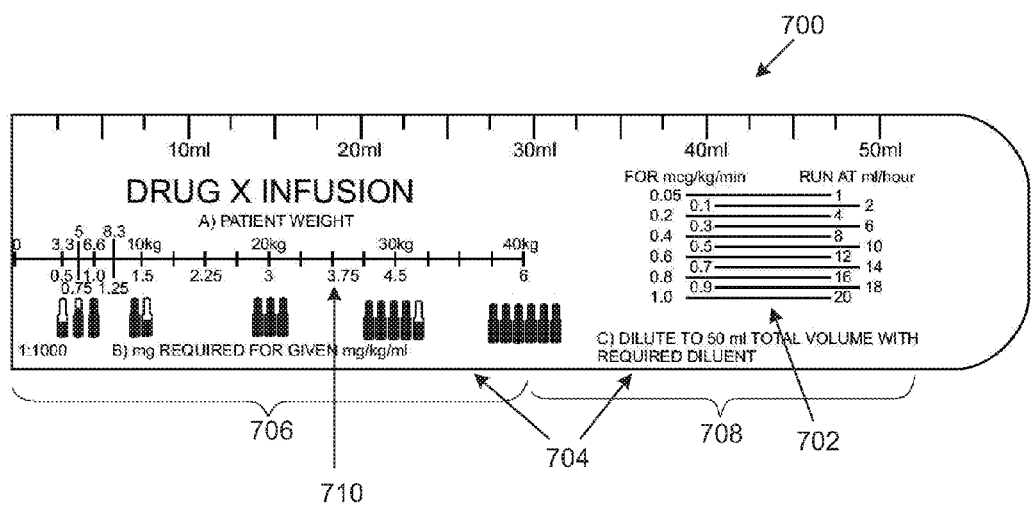

FIG. 7 illustrates a fifth embodiment of a label (700) in the form of an accessory for a syringe in accordance with the invention. In this embodiment, the label (700) includes an administration assistance table (702) in order to assist in the determination of a required rate of administration by infusion of a prepared volume of medicament for a given infusion dose.

Similarly to the label (600) illustrated in FIG. 6, the label (700) of this embodiment includes an adapted dilution scale (704) on which is displayed the total number of milligrams of medicament (706) required as well as the volume of diluent (708) required in order to prepare a mixture of a pre-calculated required total concentration in for example, mg/kg. In order to prepare the correct mixture of medicament and diluent for a given patient body weight, the medicament is drawn into the syringe according to the patient's body weight indicated on the patient body weight scale (710) and then drawing the applicable amount of diluent into the syringe, such that the rate of administration scale (702) is accurate. The required diluent may either be the volume required to fill the syringe, or a specific amount of diluent to obtain a specific concentration depending on the patient body weight and medicament concentration. To further assist a user when preparing the medicament, the label (700) provides for a required quantity of ampules which represent the required volume of medicament required for a given patient body weight.

Once the mixture has been prepared, the administration assistance table (702) may be used to determine the required rate of administration of the mixture by a syringe pump.

It will be appreciated that the administration assistance table (702) will inform the medical provider of the required rate of administration of the mixture in order to achieve a desired infusion dose, for example in micrograms per kilogram per minute (mcg/kg/min). This may be particularly useful where the equipment generally used for such procedures, such as computerised syringe pumps or syringe drivers, are not available, by introducing the mixture into a suitable vessel for infusion by a standard portable intravenous pump that electronically regulates and monitors the flow of intravenous fluid, or even simply gravity controlled dial-in flow meters.

It will be appreciated that labels in accordance with the invention will substantially eliminate the complexities typically encountered with the administration of medicaments that are dependent on more than one variable. The labels will enable non-trained users to administer medicaments by simply determining the patient's body weight and then drawing the required medicament volume into a syringe without the need of performing complex calculations.

Although printing of a body weight scale on syringes as is suggested in the prior art may alleviate some of the complexities encountered, such pre-printed syringes do not provide an effective solution to the problem currently at hand. The pre-printing of a weight scale on a syringe will require that such syringes are manufactured for every single medicament as well as every single recommended concentration which may be administered by such a syringe. Although possible, it is highly inconceivable, particularly in a third world context in which access to sophisticated equipment and technology may be limited. In addition, the manufacturing cost of a label will be but a fraction of the manufacturing cost of a syringe.

Furthermore, the provision of a label in accordance with the invention will permit manufacturing of such labels in which information is provided in any language, thereby reducing the risk of incorrect dosage preparation and or administration due to mistranslation or the like.

Further, required medicament dosages may also vary according to the route of administration of the medicament. Thus, for example, where the medicament is administered orally to the patient, a particular volume of medicament may be required, while intravenous administration of the medicament may require a different volume. Similarly, in cases where a medicament may be used for more than one purpose, the concentration thereof or medicament and diluent mixture concentration may be different. Providing a medicament with a number of labels in accordance with the invention may effectively solve these problems as labels could be provided for any route of administration or any use of the medicament and a user of the medicament can simply adhere the appropriate label to the syringe.

It will be appreciated that many other potential embodiments of this syringe accessory system exist which fall within the scope of the invention, particularly regarding the shape and configuration thereof. Thus, for example, the calibration of the patient weight scale or dilution assistance scale may vary depending on the route of administration or the use of the medicament. It will be appreciated that the label in accordance with the invention could be easily modified to accommodate such variations without departing from the scope of the invention.

In addition, it will be appreciated that the use of labels in accordance with the invention is not limited to the administration of a medicament to humans, but could also be used for the administration of medicaments to animals and the like.

The volume and weight indications on the labels of FIGS. 1 to 7 are for illustration purposes only, and the indications will vary according to the type of medicament, the syringe size or the like. Furthermore, a syringe label of the invention may be used for any type or form of syringe by simply manufacturing a label with the correctly calibrated patient weight and volume indication scales according to the size of the syringe used. The risk of putting a label on an incorrect syringe size is low because such a label will not have its volume indication scale align with the syringe's volume indication scale.

The invention claimed is:

1. A label in the form of an accessory for a manufactured syringe that has graduations corresponding to volumes within the syringe, the label comprising a flexible generally rectangular elongate sheet of material with adhesive provided on an operatively back surface thereof, the sheet having two parallel major edges extending along the length of the elongate sheet, wherein a first scale is provided so as to be visible from an operatively front surface of the label along one of the major edges, the first scale being a volume indication scale calibrated to align with an existing volume indication scale on the syringe, and a second scale is provided adjacent the volume indication scale, the second scale being a scale that relates to a patient body weight scale, the patient body weight scale being calibrated so that a correct recommended dose as a volume of a medicament can be delivered to a patient of a given weight, either during administration of the medicament or during preparation of a mixture to be administered, by aligning a stopper of the syringe with the patient weight indicated by the patient weight scale, and wherein the label displays a type and a concentration of the medicament to be held by the syringe, a recommended dose of the medicament, and a recommended route of administration.

2. A label as claimed in claim 1 in which the label is colour-coded according to international colour coding systems used for labels to indicate the type of medicament to be held in the syringe.

3. A label as claimed in claim 1 in which the relationship between the volume indication scale and the patient weight scale is of a linear or non-linear relationship as determined by the recommended dosage characteristics of the medicament.

4. A label as claimed in claim 1 in which the patient body weight scale is aligned with the volume indication scale so that the weight indications on the scale increase in line with the volume indications on the volume indication scale.

5. A label as claimed in claim 1 in which the patient body weight scale is inversely aligned with the volume indication scale, so that the weight indications on the patient body weight scale decrease as the volume indications on the volume indication scale increase.

6. A label as claimed in claim 1 in which one of the parallel major edges of the label has a dilution assistance scale to indicate the volume of medicament and the volume of diluent required for a recommended concentration of the mixture.

7. A label as claimed in claim 1 in which the label includes a bolus scale, which may be used to administer a constant dose of medicament or medicament and diluent mixture in a bolus fashion wherein the patient weight scale may be used to draw a required volume of medicament into the syringe and the syringe may then be filled with a diluent for a recommended concentration, which may then be administered according to the fixed volumes indicated by the bolus scale.

8. A label as claimed in claim 1 in which the label includes an administration assistance table for the determination of a required rate of administration of a concentration of medicament, wherein the patient weight scale may be used to draw a required volume of medicament into the syringe and the syringe may then be filled with a diluent for a recommended concentration, which may then be administered according to the required rate of administration in order to achieve a required mcg/kg/min dose target.

9. A label as claimed in claim 1 in which the label is opaque.

10. A label as claimed in claim 1 in which the label is transparent or partially transparent.

11. A syringe having a label applied to it, the label carrying indicia including a first scale, the first scale being a volume indication scale calibrated to align with an existing volume indication scale on the syringe, and a second scale adjacent the volume indication scale, the second scale being a patient body weight scale calibrated so that a correct recommended dose as a volume of a medicament can be delivered to a patient of a given weight, either during administration of the medicament or during preparation of a mixture to be administered, by aligning a stopper of the syringe with the patient weight indicated by the patient weight scale, and wherein the label displays a type and a concentration of the medicament to be held by the syringe, a recommended dose of the medicament, and a recommended route of administration.

* * * * *